(12) United States Patent
Walters et al.

(10) Patent No.: US 7,371,561 B2
(45) Date of Patent: May 13, 2008

(54) IN VITRO, MULTIPLE ELECTRODE PAIR ARRAY AND MULTIPLE TREATMENT CELL APPARATUS FOR USE IN ELECTROPORATION

(75) Inventors: Richard E. Walters, Columbia, MD (US); Paul K. Gustavson, Gambrills, MD (US)

(73) Assignee: Cyto Pulse Sciences, Glen Burnie, MD (US)

( * ) Notice: Subject to any disclaimer, the term of this patent is extended or adjusted under 35 U.S.C. 154(b) by 680 days.

(21) Appl. No.: 10/694,345

(22) Filed: Oct. 28, 2003

(65) Prior Publication Data
US 2005/0089992 A1   Apr. 28, 2005

(51) Int. Cl.
*C12M 1/42* (2006.01)
(52) U.S. Cl. .............................. 435/285.2; 435/288.4; 435/305.2; 422/82.02; 422/102; 324/450; 324/692
(58) Field of Classification Search ............. 435/285.2, 435/287.1, 288.4; 422/82.01, 82.02
See application file for complete search history.

(56) References Cited
U.S. PATENT DOCUMENTS

| | | | | |
|---|---|---|---|---|
| 4,695,547 A | * | 9/1987 | Hilliard et al. .......... | 435/285.2 |
| 5,187,096 A | * | 2/1993 | Giaever et al. .......... | 435/287.1 |
| 5,643,742 A | * | 7/1997 | Malin et al. ................... | 435/29 |
| 6,117,660 A | * | 9/2000 | Walters et al. ........... | 435/173.6 |
| 6,352,853 B1 | * | 3/2002 | King et al. .............. | 435/285.2 |
| 2002/0025573 A1 | * | 2/2002 | Maher et al. ............ | 435/287.1 |

* cited by examiner

*Primary Examiner*—William H. Beisner
(74) *Attorney, Agent, or Firm*—Marvin S. Townsend

(57) ABSTRACT

A multiple electrode pair array apparatus is provided for use with a multiple well plate which has multiple wells distributed in a two-dimensional matrix array which has R rows and C columns. The multiple electrode pair array apparatus includes a non-conductive base member. An array of pairs of electrodes are attached to the base member and project therefrom. The pairs of electrodes are distributed on the base member in a two-dimensional matrix array which has R rows and C columns to enable registration with the two-dimensional matrix array of wells. Each pair of electrodes includes a respective first electrode and a respective second electrode. An array of R row conductors are electrically connected to corresponding first electrodes. An array of C column conductors are oriented perpendicular to the R row conductors, are electrically insulated from the row conductors, and are electrically connected to corresponding second electrodes.

6 Claims, 4 Drawing Sheets

IN VITRO, MULTIPLE ELECTRODE PAIR ARRAY AND MULTIPLE TREATMENT CELL APPARATUS FOR USE IN ELECTROPORATION

CROSS-REFERENCE TO RELATED APPLICATION

The present patent application is related to another patent application entitled APPARATUS FOR RECEIVING AND ALIGNING A MULTIPLE ELECTRODE PAIR ARRAY AND A MULTIPLE TREATMENT CELL FOR USE IN ELECTROPORATION by Walters et al, which is filed concurrently with the present application.

TECHNICAL FIELD

The present invention relates to the field of electroporation. More specifically, the present invention is especially concerned with an electrode array for use with treatment wells used in electroporation.

BACKGROUND ART

U.S. patent application Publication No. US 2003/0070939 of Walters et al, published Apr. 17, 2003, which was ultimately based upon PCT International Application PCT/US97/09300, of Walters et al, filed Jun. 1, 1997, and published as PCT International Publication Number WO 98/56893 on Dec. 17, 1998, discloses a method and apparatus for treating materials with electrical fields having varying orientations. In FIG. 13, of both the originally filed PCT application and the published PCT application, an array of eight in vitro test wells is disclosed. As disclosed on page 54 of the PCT International Publication Number WO 98/56893, each test well can be pulsed in a desired way either different from or the same as other test wells. Moreover, on page 53 of the PCT published application, there is a disclosure that generally, N applied pulses can be routed to N groups of electrodes in sequence. Furthermore, successive groups of electrodes in the N groups of electrodes can be comprised of different individual electrodes. Alternatively, successive groups of electrodes in the N groups of electrodes can be comprised of the same individual electrodes. Clearly, the disclosures in PCT International Publication Number WO 98/56893, published on Dec. 17, 1998, provide high throughput of electroporation tests or treatments. The array of test wells in FIG. 13 can be regarded as either a matrix array having one row and eight columns, or, alternatively, a matrix array having eight rows and one column.

It is noted that the disclosures in PCT International Publication Number WO 98/56893 are contained in U.S. Pat. No. 6,117,660 of Walters et al, which is incorporated herein by reference. U.S. Pat. No. 6,117,660 was issued on Sep. 12, 2000.

U.S. Pat. No. 6,352,853 of King et al, issued Mar. 5, 2002, based upon a utility patent application filed Nov. 16, 1999, which was related to a provisional patent application filed Dec. 7, 1998, discloses multi-channel electrode arrays used in electroporation. U.S. Pat. No. 6,352,853 discloses that multi-channel electrode systems are used for high throughput introduction of exogenous molecules into cells, or to avoid the need for transferring cells from culture containers to electroporation cuvettes. A multi-channel electroporation apparatus includes a plurality of pairs of electrodes positioned in respective ones of a plurality of chambers that hold the exogenous materials and the cells. U.S. Pat. No. 6,352,853 discloses that multi-channel electroporation devices contain 8 or 96 pairs of coaxial electrodes (Genetronics, Inc., San Diego, Calif.). These devices are used for electroporation in standard 96-well plates, which consist of 8 rows and 12 columns of wells and have a standard size of about 8.5 (W) cm.times.12.7 cm (L), with a standard center-to-center spacing of 9.0 mm between wells. For a standard 96 well plate, there are 96 wells, 96 pairs of electrodes (one pair of electrodes for each well), 96 first electrode conductors, and 96 second electrode conductors. Thus, there are 192 first or second electrode conductors to connect to 96 pairs of electrodes for 96 wells. The complexity involved with 192 first or second electrode conductors for a standard 96 well plate is very high. Moreover, the electronic apparatus that is needed to connect to and drive the 192 first or second electrode conductors is also very high. In this respect, it would be desirable to provide an electroporation apparatus that considerably reduces the complexity with respect to 192 first or second electrode conductors and the complexity with respect to the electronic apparatus needed to connect with and drive 192 first or second electrode conductors for a standard 96 well plate used for electroporation. More generally, it would be desirable if an electroporation apparatus were provided in which the number of conductors connected with electrodes for electroporation were considerably less than the number of electrodes.

Parenthetically, it is believed by the inventors of this present patent application that the Genetronics devices referred to in U.S. Pat. No. 6,352,853 have been superseded by BTX Products discussed herein below.

Further with respect to U.S. Pat. No. 6,352,853, electrodes are disclosed wherein each electrode includes a 24 electrode teeth. Each electrode is connected either to a positive (+) electric potential or to a negative (−) electric potential. Each row of 24 wells in a standard 384 well plate receives one 24 teeth electrode connected to a positive (+) electric potential and one 24 teeth electrode connected to a negative (−) electric potential. With the electroporation system provided in U.S. Pat. No. 6,352,853, a full row of 24 wells is treated simultaneously. There are 16 rows of 24 wells. Therefore, there are 32 electrodes needed to accommodate the 16 rows. Therefore, U.S. Pat. No. 6,352,853 has found a way to reduce the number of electrodes for treating all of the wells in a 384 well plate from 768 conductors to 32 conductors.

Yet, with U.S. Pat. No. 6,352,853, there is no way to electrically treat any one of the 24 wells in a full row of 24 well any differently from any other well in the full row of 24 wells. Since there are 16 rows of wells in a standard 384 well plate, only 16 different modalities of electrical treatment can be applied to the 384 wells. Stated differently, with U.S. Pat. No. 6,352,853, the individual wells are not individually addressable. To provide greater versatility, it would be desirable to provide an electroporation apparatus in which 384 electrode pairs in all 384 wells in a standard 384 well plate can be treated with a different electrical modality without the need for 768 conductors for connection with 364 pairs of electrodes. More generally, it would be desirable if an electroporation apparatus were provided in which pairs of electrodes in all wells in a standard well plate can be treated with a different electrical modality without the need for a pair of electrical conductors for each electrode pair. Stated somewhat differently, it would be desirable if individual wells in a standard well plate could be individually addressable.

With respect to BTX Products, a printout of ten pages from an Internet web site for BTX Products, having a URL of http://www.btxonline.com, which were printed on Dec. 16, 2002, include a three page description of HT-3000 High Throughput Electroporation Generator, a one page image of HT-3000, a two page description of Electroporation Plate Handlers, a one page image of HT-200, a one page description of Electroporation Plates, and a one page description of Transfection Optimization Software. The BTX Electroporation Plates use gold-plated, disposable multi-well electroporation plates which are used with high throughput electroporation apparatus. Such BTX gold-plated, disposable multi-well electroporation plates are quite expensive, considering the effort and expensive materials used to produce them. In essence, these BTX gold-plated, disposable multi-well electroporation plates provide both multiple electrodes and multiple wells in an integrated unit. Therefore, when the BTX gold-plated, disposable multi-well electroporation plates are disposed of, both the multiple electrodes and the multiple wells are disposed of at the same time. In this respect, it would be desirable for an electroporation apparatus to be provided in which multiple electrodes are not disposed of when multiple wells are disposed of.

On the other hand, simple, plastic disposable multi-well plates are well known and are much less expensive to make and use than the BTX gold-plated, disposable multi-well electroporation plates. Yet, it is not known that such well known simple, plastic disposable multi-well plates are used as wells in which multiple electroporations are carried out. In this respect, it would be desirable for an electroporation apparatus to be provided in which simple, plastic disposable multi-well plates can be employed and disposed of readily.

Returning to U.S. Pat. No. 6,352,853, this patent discloses a number of ways in which the electrode combs are supported. Yet, in each way of electrode comb support, once the electrode combs have been placed in the respective wells of a standard well plate, access to the respective wells is prevented by the support structure for the electrode combs. There may be times when it would be desirable to access the respective wells of a standard well plate even after electrodes have been placed in the respective wells. Generally, therefore, it would be desirable to provide a support for electrodes that are placed in the wells of a standard well plate wherein the electrode support allows access to the wells with the electrodes positioned in the wells.

Each well in a standard 96 rectangular well plate has a predetermined well volume. When pairs of rectangular electrodes are placed into the wells, the predetermined volumes are reduced, thereby leaving a reduced volume for conducting electroporation of materials. To assure that the predetermined volumes are reduced to a minimum by the electrodes so that the remaining volumes available for electroporation are at a maximum, it would be desirable if pairs of rectangular electrodes were placed into the rectangular wells so that the rectangular electrodes closely fit against adjacent walls of the wells.

Thus, while the foregoing body of prior art indicates it to be well known to use a matrix array of pairs of electrodes for a well plate which includes a matrix array of wells, the prior art described above does not teach or suggest a multiple electrode pair array which has a two-dimensional matrix array of electrode conductors and which has the following combination of desirable features: (1) provides an electroporation apparatus that considerably reduces the complexity with respect to 192 first or second electrode conductors and the complexity with respect to the electronic apparatus needed to drive 192 first or second electrode conductors for a 96 well plate used for electroporation; (2) provides an electroporation apparatus in which the number of conductors connected with electrodes for electroporation is considerably less than the number of electrodes; (3) provides an electroporation apparatus in which 384 electrode pairs in all 384 wells in a 384 well plate can be treated with a different electrical modality; (4) provides an electroporation apparatus in which all pairs of electrodes in all wells in a well plate can be treated with a different electrical modality without the need for a pair of electrical conductors for each electrode pair; (5) provides an electroporation apparatus in which multiple electrodes are not disposed of when a multiple well plate is disposed of; (6) provides an electroporation apparatus in which simple, plastic disposable multi-well plates can be employed and disposed of readily; (7) provides a support for electrodes that are placed in the wells of a standard well plate wherein the electrode support allows access to the wells when the electrodes are positioned in the wells; and (8) provides that pairs of rectangular electrodes are placed into the rectangular wells of a multi-well plate so that the rectangular electrodes closely fit against adjacent walls of the wells. The foregoing desired characteristics are provided by the unique multiple electrode pair array of the present invention as will be made apparent from the following description thereof. Other advantages of the present invention over the prior art also will be rendered evident.

DISCLOSURE OF INVENTION

To achieve the foregoing and other advantages, the present invention, briefly described, a multiple electrode pair array apparatus is provided for use with a multiple well plate which has multiple wells distributed in a two-dimensional matrix array which has R rows and C columns. The multiple electrode pair array has a two-dimensional matrix array of electrode conductors. The multiple electrode pair array apparatus includes a non-conductive base member. An array of pairs of electrodes are attached to the base member and project therefrom. The pairs of electrodes are distributed on the base member in a two-dimensional matrix array which has R rows and C columns to enable registration with the two-dimensional matrix array of wells. Each pair of electrodes includes a respective first electrode and a respective second electrode. An array of R row conductors are attached to the non-conductive base member, wherein each row conductor is electrically connected to corresponding first electrodes in a corresponding row of first electrodes. An array of C column conductors are attached to the non-conductive base member. The C column conductors are oriented perpendicular to the R row conductors. Each column conductor is electrically insulated from the row conductors, and each column conductor is electrically connected to corresponding second electrodes in a corresponding column of second electrodes.

Preferably, the first electrodes and the second electrodes are parallel to each other; the first electrodes and the R row conductors are parallel to each other; and the second electrodes and the C column conductors are perpendicular to each other.

The non-conductive base member can be made from durable, plastic, water-resistant, conventional circuit board stock. The first electrodes and the second electrodes can be bonded to the non-conductive base member by conventional techniques. The row conductors and the column conductors can be formed on the non-conductive base member by conventional techniques. The row electrical connection members and the column electrical connection members can be electrically connected to the respective row conductors and to the respective column conductors by conventional techniques. Preferably, the materials comprising the multiple electrode pair array apparatus of the invention are made from materials that are resistant to heating from repeated sterilization events. Often, the multiple electrode pair array apparatus of the invention is sterilized before being attached to a conventional multi-well plate.

The non-conductive base member has a top portion and a bottom portion. Preferably, the row conductors and the column conductors are positioned away from the top portion of the non-conductive base member. In this respect, the top portion of the non-conductive base member is insulated from the row conductors and the column conductors. As a result, a user is prevented from coming into contact with the row conductors and the column conductors, thereby protecting the user from electrical shock.

Preferably, an adjacent electrode pair spacing gap is provided between a first electrode on one pair of electrodes and a second electrode on an adjacent pair of electrodes, such that an inside wall of the multiple well plate is received in the adjacent electrode pair spacing gap. More specifically, the respective inside walls of the multiple well plate are received in the respective adjacent electrode pair spacing gaps by relatively tight friction fits. As a result, the respective first electrodes and the respective second electrodes fit tightly against the respective inside walls, thereby leaving a maximum amount of space for sample reception and electroporation in the respective wells of the multiple well plate.

The amount of frictional resistance needed to be overcome in order to provide a tight fit between a 96 electrode pair matrix array of the invention and a conventional 96 well multiple well plate can be quite substantial. The tight fit permits the respective electrode pairs in the electrode pair matrix array to provide uniform electric fields in the respective wells and to prevent material from getting behind the respective electrodes between the respective electrodes and the inside walls of the multiple well plate.

Conversely, there is a substantial amount of frictional resistance to overcome to remove a 96 electrode pair matrix array of the invention that has been fitted into a 96 well multiple well plate.

Preferably, a set of row electrical connection members are electrically connected to the row conductors, and a set of column electrical connection members are electrically connected to the column conductors.

Preferably, the base member includes a plurality of access channels which are in registration with the wells of the multiple well plate.

Preferably, the access channels are circular in shape. For a 96 multiple electrode pair array with a two-dimensional matrix array of electrode conductors of the invention, for use with a conventional 96 well multiple well plate which has rectangular wells, the access channels can be 7 mm. in diameter. Respective access channels are located between respective first electrodes and respective second electrodes in the respective electrode pairs.

Once the multiple electrode pair array apparatus of the invention has been fitted into the multiple well plate, the contents of each respective well in the multiple well plate can be modified through the respective access channels. Pressure pipettes can be used to add material to the respective wells, and suction pipettes can be used to remove material from the respective wells. The presence of the access channels provide an additional benefit. The access channels eliminate cross contamination between wells in the multiple well plate that can occur if the electrode pair matrix array is inserted into the wells after the wells have been filled with liquid solution.

In operating the multiple electrode pair array with the two-dimensional matrix array of electrode conductors of the invention in conjunction with a multiple well plate, each electrode pair and consequently each well is individually addressable. As a result, a wide variety of modalities of electric field application can be employed. For example, if desired, each well in the multiple well plate can have a unique electric field treatment. That is, for a 96 well multiple well plate, there can be 96 different experiments or treatments conducted simultaneously. Alternatively, if desired all 96 could be treated with the same electric field treatment. Also, a wide number of additional variations of electric treatment can also be employed.

It is, therefore, an object of the present invention is to provide a multiple electrode pair array which provides an electroporation apparatus that considerably reduces the complexity with respect to 192 first or second electrode conductors and the complexity with respect to the electronic apparatus needed to drive 192 first or second electrode conductors for a 96 well plate used for electroporation.

Still another object of the present invention is to provide a multiple electrode pair array that provides an electroporation apparatus in which the number of conductors connected with electrodes for electroporation is considerably less than the number of electrodes.

Yet another object of the present invention is to provide a multiple electrode pair array which provides an electroporation apparatus in which 384 electrode pairs in all 384 wells in a 384 well plate can be treated with a different electrical modality.

Even another object of the present invention is to provide a multiple electrode pair array that provides an electroporation apparatus in which all pairs of electrodes in all wells in a well plate can be treated with a different electrical modality without the need for a pair of electrical conductors for each electrode pair.

Still a further object of the present invention is to provide a multiple electrode pair array which provides an electroporation apparatus in which multiple electrodes are not disposed of when a multiple well plate is disposed of.

Yet another object of the present invention is to provide a multiple electrode pair array that provides an electroporation apparatus in which simple, plastic disposable multi-well plates can be employed and disposed of readily.

Still another object of the present invention is to provide a multiple electrode pair array which provides a support for electrodes that are placed in the wells of a standard well plate wherein the electrode support allows access to the wells when the electrodes are positioned in the wells.

Yet another object of the present invention is to provide a multiple electrode pair array that provides that pairs of rectangular electrodes are placed into the rectangular wells of a multi-well plate so that the rectangular electrodes closely fit against adjacent walls of the wells.

With the present invention, a wide variety of biological materials can be electroporated in vitro. Such biological materials include membrane-containing material which can include cells, tissues, organs, and liposomes.

Additional biological materials include, but are not limited to, microscopic or submicroscopic vesicles that contain lipid or fatty acid membrane, e.g., prokaryotic and eukaryotic cells, microsomes, and micelles. The vesicles can be unilamellar, bilamellar or multilamellar and range in size, e.g., from 1 nm to 100 mu·m.

When the electrodes are arrayed as two electrodes located on opposite sides of an individual well in which biological cells are being subject to electroporation, the direction of the electric fields in a sequence of pulses applied to the electrodes can be sequentially reversed, whereby electroporation is improved.

BRIEF DESCRIPTION OF DRAWINGS

The invention will be better understood and the above objects as well as objects other than those set forth above will become more apparent after a study of the following detailed description thereof. Such description makes reference to the annexed drawing wherein.

MODE FOR CARRYING OUT THE INVENTION

Figure 1:
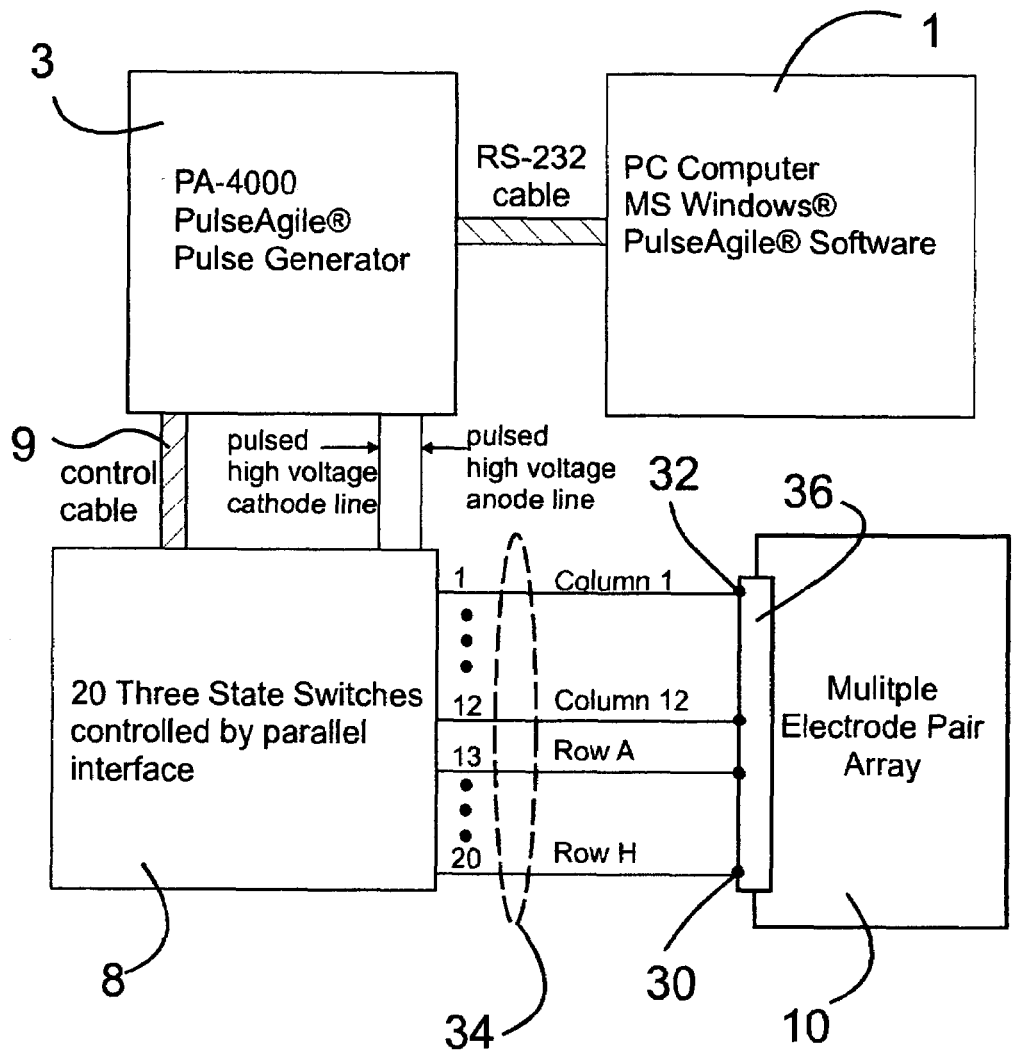
FIG. 1 is a block diagram of the overall electroporation system used to drive the multiple electrode pair array and the two-dimensional matrix array of electrode conductors of the invention.

With reference to the drawings, a multiple electrode pair array apparatus 10 embodying the principles and concepts of the present invention will be described.

The multiple electrode pair array apparatus 10 is provided for use with a multiple well plate 11 which has multiple wells distributed in a two-dimensional matrix array which has R rows and C columns. The multiple electrode pair array apparatus 10 includes a non-conductive base member 12. An array of pairs of electrodes 93 are attached to the base member 12 and project therefrom. The pairs of electrodes are distributed on the base member 12 in a two-dimensional matrix array which has R rows 16 and C columns 18 to enable registration with the two-dimensional matrix array of wells. Each pair of electrodes includes a respective first electrode 20 and a respective second electrode 22. An array of R row conductors 24 are attached to the non-conductive base member 12, wherein each row conductor 24 is electrically connected to corresponding first electrodes 20 in a corresponding row of first electrodes 20. An array of C column conductors 26 are attached to the non-conductive base member 12. The C column conductors 26 are oriented perpendicular to the R row conductors 24. Each column conductor 26 is electrically insulated from the row conductors 24, and each column conductor 26 is electrically connected to corresponding second electrodes 22 in a corresponding column of second electrodes 22.

Preferably, the first electrodes 20 and the second electrodes 22 are parallel to each other; the first electrodes 20 and the R row conductors 24 are parallel to each other; and the second electrodes 22 and the C column conductors 26 are perpendicular to each other.

The non-conductive base member 12 can be made from durable, plastic, water-resistant, conventional circuit board stock. The first electrodes 20 and the second electrodes 22 can be bonded to the non-conductive base member 12 by conventional techniques. The row conductors 24 and the column conductors 26 can be formed on the non-conductive base member 12 by conventional techniques. The row electrical connection members 30 and the column electrical connection members 32 can be electrically connected to the respective row conductors 24 and to the respective column conductors 26 by conventional techniques.

Preferably, the materials comprising the multiple electrode pair array apparatus 10 of the invention are made from materials that are resistant to heating from repeated sterilization events. Often, the multiple electrode pair array apparatus 10 of the invention is sterilized before being attached to a conventional multi-well plate.

The non-conductive base member 12 has a top portion and a bottom portion. Preferably, the row conductors 24 and the column conductors 26 are positioned away from the top portion of the non-conductive base member 12. In this respect, the top portion of the non-conductive base member 12 is insulated from the row conductors 24 and the column conductors 26. As a result, a user is prevented from coming into contact with the row conductors 24 and the column conductors 26, thereby protecting the user from electrical shock.

Each of the multiple electrode pair array apparatus 10 and the multiple well plate 11 include alignment structures to assure proper registration between the multiple electrode pair array apparatus 10 of the invention and the multiple well plate 11 when the multiple electrode pair array apparatus 10 is connected to the multiple well plate 11. The respective alignment structures assure that there is a one-to-one correspondence between the respective locations of the pairs of electrodes in the two-dimensional matrix array electrode pairs and the locations of the wells in the two-dimensional matrix array of wells in the multiple well plate 11.

Figure 3:
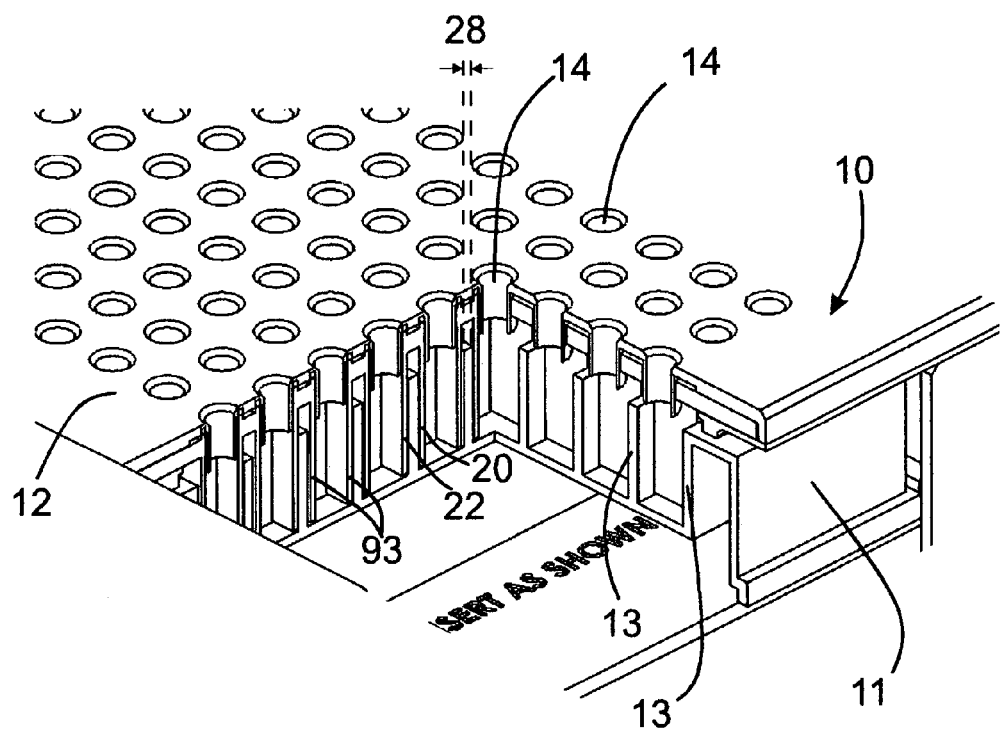
FIG. 3 is a partially cut away perspective view showing a multiple electrode pair array in-place in a standard 96 rectangular well plate.

As shown in FIG. 3, adjacent electrode pair spacing gap 28 is provided between a first electrode 20 on one pair of electrodes and a second electrode 22 on an adjacent pair of electrodes, such that an inside wall 13 of the multiple well plate 11 is received in the adjacent electrode pair spacing gap 28. More specifically, the respective inside walls 13 of the multiple well plate 11 are received in the respective adjacent electrode pair spacing gaps 28 by relatively tight friction fits. As a result, the respective first electrodes 20 and the respective second electrodes 22 fit tightly against the respective inside walls 13, thereby leaving a maximum amount of space for sample reception and electroporation in the respective wells of the multiple well plate 11.

The amount of frictional resistance needed to be overcome in order to provide a tight fit between a 96 electrode pair matrix array of the invention and a conventional 96 well multiple well plate 11 can be quite substantial. The tight fit permits the respective electrode pairs in the electrode pair matrix array to provide uniform electric fields in the respective wells and to prevent material from getting behind the respective electrodes between the respective electrodes and the inside walls 13 of the multiple well plate 11.

Conversely, there is a substantial amount of frictional resistance to overcome to remove a 96 electrode pair matrix array of the invention that has been fitted into a 96 well multiple well plate 11.

Filed concurrently herewith is a patent application entitled APPARATUS FOR RECEIVING AND ALIGNING A MULTIPLE ELECTRODE PAIR ARRAY AND A MULTIPLE TREATMENT CELL FOR USE IN ELECTROPORATION by Walters et al which sets forth an apparatus for fitting together a multiple electrode pair array apparatus 10 of the invention and a multiple well plate 11 and for separating a multiple electrode pair array apparatus 10 of the invention from a multiple well plate 11.

Preferably, a set of row electrical connection members 30 are electrically connected to the row conductors 24, and a set of column electrical connection members 32 are electrically connected to the column conductors 26.

As shown in FIG. 3, preferably, the base member 12 includes a plurality of access channels 14 which are in registration with the wells of the multiple well plate 11.

Preferably, the access channels 14 are circular in shape. For a 96 multiple electrode pair array with a two-dimensional matrix array of electrode conductors of the invention, for use with a conventional 96 well multiple well plate 11 which has rectangular wells, the access channels 14 can be 7 mm. in diameter.

Once the multiple electrode pair array apparatus 10 of the invention has been fitted into the multiple well plate 11, the contents of each respective well in the multiple well plate 11 can be modified through the respective access channels 14. Pressure pipettes can be used to add material to the respective wells, and suction pipettes can be used to remove material from the respective wells. The presence of the access channels 14 provide an additional benefit. The access channels 14 eliminate cross contamination between wells in the multiple well plate 11 that can occur if the electrode pair matrix array is inserted into the wells after the wells have been filled with liquid solution.

Figure 4:
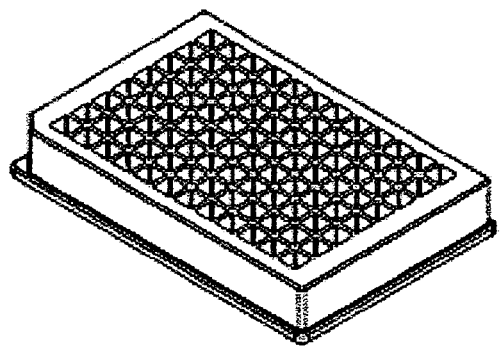
FIG. 4 is a perspective view of a PRIOR ART standard 96 rectangular well plate.
Figure 5:
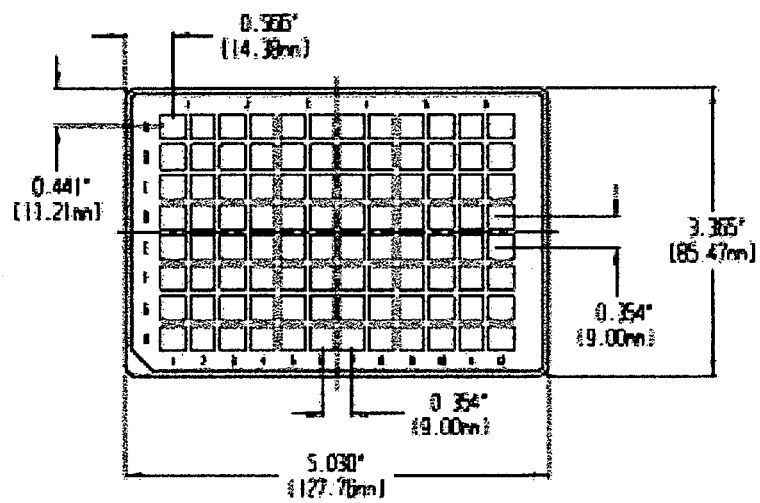
FIG. 5 is a top view of the PRIOR ART standard 96 rectangular well plate shown in FIG. 4.
Figure 6:
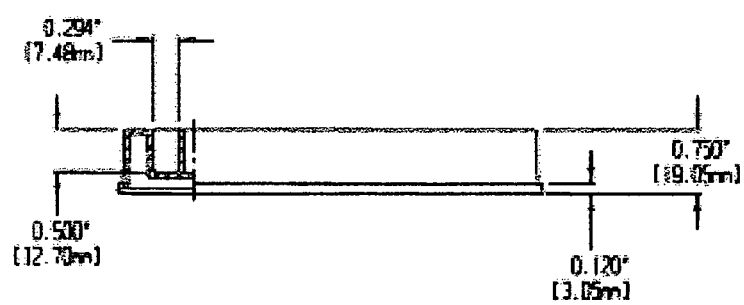
FIG. 6 is a partial cross-sectional view of the standard 96 rectangular well plate shown in FIG. 5 taken along line 6-6 thereof.

FIGS. 4, 5, and 6 show a number of views of a conventional 96 rectangular well multiple well plate 11 that is registerable with a 96 multiple electrode pair array with a two-dimensional matrix array of electrode conductors of the invention. In this respect, the adjacent electrode pair spacing gap 28 is approximately equal to the thickness of the inside walls 13 of the respective wells.

FIG. 1 shows the PA-4000 electroporation system, of Cyto Pulse Sciences, Inc., Hanover, Md., USA, which is configured with the Programmable Pulse Switch 8. More disclosures about the structure and the operation of the electroporation system of Cyto Pulse Sciences, Inc. are disclosed in U.S. Pat. No. 6,010,613 of Walters et al, incorporated herein by reference. A control cable 9 is used to control the Programmable Pulse Switch 8. The Programmable Pulse Switch 8 has 20 output conductor lines which include eight row conductor lines A through H and which include twelve column conductor lines 1 thru 12. The eight row conductor lines A through H and the twelve column conductor lines 1 thru 12 from the Programmable Pulse Switch Cabinet 8 to the multiple electrode pair array apparatus 10 can be in form of a row/column conductor cable 34. The row/column conductor cable 34 can terminate at row/column conductor plug 36 which is electrically connected to the respective row and column conductor lines in the row/column conductor cable 34. The row/column conductor plug 36 can include respective conductor contact elements which form electrical connections with the respective row electrical connection members 30 and the column electrical connection members 32 of the multiple electrode pair array apparatus 10. The 20 output conductor lines are set to one and only one of three states, pulse out, pulse return, no connection.

The overall electroporation system consists of three cabinets: (1) the compatible PC 1; (2) the PA-4000 cabinet 3 which contains the control microprocessor, the Interface-Control Assembly, the High Voltage Assembly, the High Voltage Power Supply, and the low voltage power supply; and (3) the Programmable Pulse Switch Cabinet 8.

More detailed operation of the overall electroporation system is explained in the above-mentioned U.S. Pat. No. 6,117,660 of Walters et al, which is incorporated herein by reference.

The row conductor lines A through H of the Programmable Pulse Switch Cabinet 8 are electrically connected to the respective row electrical connection members 30 of the multiple electrode pair array apparatus 10. The column conductor lines 1-12 of the Programmable Pulse Switch Cabinet 8 are electrically connected to the respective column electrical connection members 32 of the multiple electrode pair array apparatus 10.

By appropriate programming by a user, any specific electrode pair in the matrix array of 96 electrode pairs can be selected for applying an electric field therein for a selected period of time and for a selected pulse pattern.

Each of the 96 electrode pairs is located at a location identified by a row position and a column position in the two-dimensional multiple electrode pair array. To select a specific electrode pair, the corresponding row conductor 24 for the first electrode 20 of the specific electrode pair and the corresponding column conductor 26 for the second electrode 22 of the specific electrode pair are energized from signals sent from the Programmable Pulse Switch Cabinet 8. As a result, the only electrode pair energized is the specific electrode pair located at the intersection of the specific row conductor and the specific column conductor that are energized by the Programmable Pulse Switch Cabinet 8.

Figure 2:
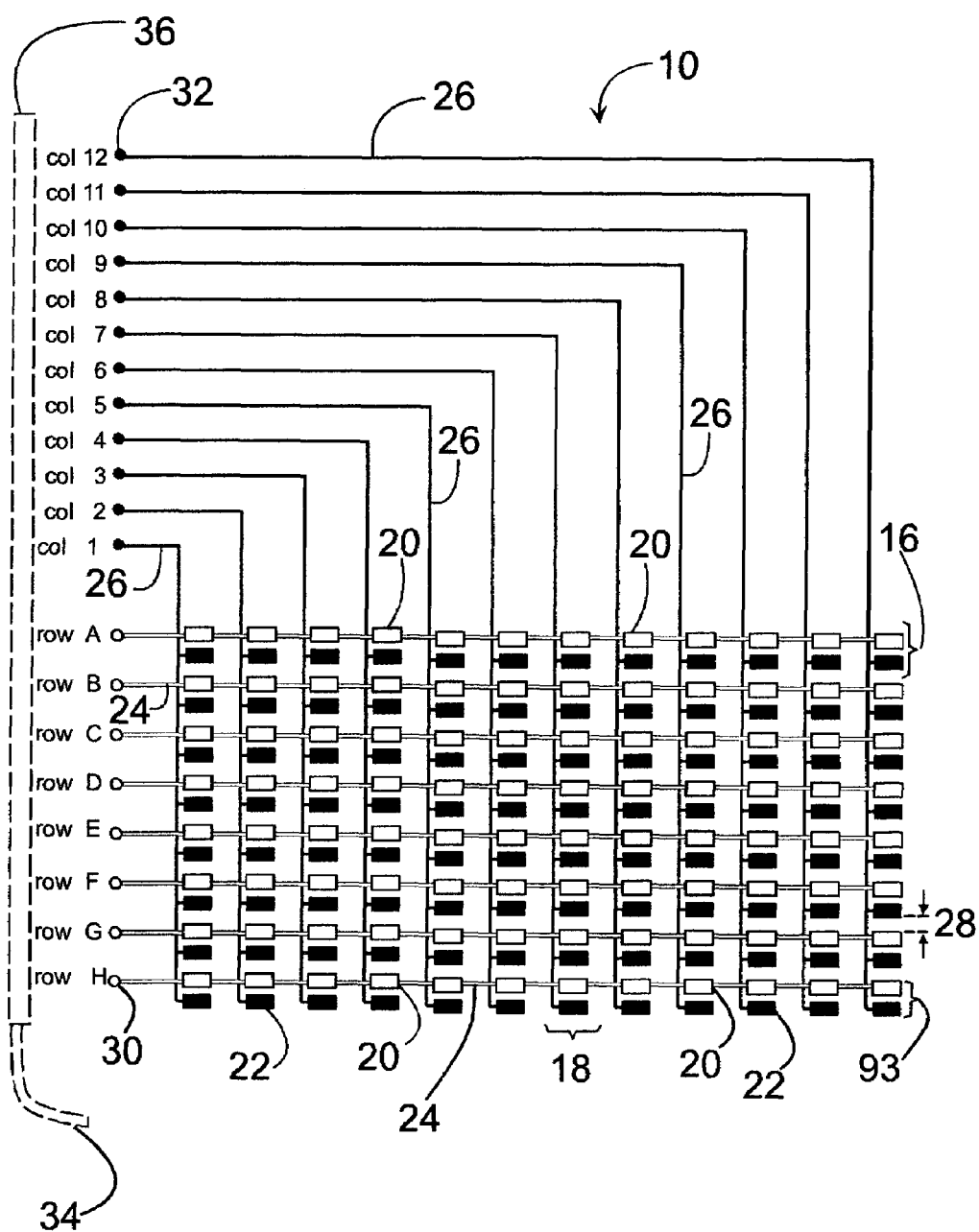
FIG. 2 is a schematic diagram of a two-dimensional matrix array of 20 matrix conductors (8 row conductors and 12 column conductors) to connect with 96 pairs of electrodes in a matrix array of electrodes (having 8 rows of electrode pairs and 12 columns of electrode pairs) for a 96 well plate.

A specific example is illustrated in FIG. 2. An electrode pair is energized (as indicated by the broken encircling line) at location Row D, Column 6. That is, the Programmable Pulse Switch Cabinet 8 is energizing the row conductor 24 corresponding to the third row in the multiple electrode pair matrix array and is energizing the column conductor 26 corresponding to the sixth column in the multiple electrode pair matrix array. As a result, only the single specific electrode pair located at Row D, Column 6 is energized.

By using the principles of the invention which include employing a two-dimensional matrix array of electrode conductors, great economies are achieved with respect to the number of conductor lines that are connected to electrode pairs when compared to a conventional arrangement of a unique pair of conductors for connection to each electrode pair. Such economies are demonstrated in Table 1 and Table 2 below.

In Table 1 below, each row in the table shows a comparison of the number of first and second conductors that are required for respective pairs of electrodes for a respective multi-well plate in contrast with the number of matrix conductors that are required for the same pairs of electrodes for the same respective multi-well plate.

For example, in Table 1, for a 96 well plate, using a conventional unique pair of first and second conductors for each of the 96 pairs of electrodes for the 96 wells, there are 192 first and second electrodes required. In contrast, for a 96 well plate, using a matrix of conductors of the invention for the 96 pairs of electrods for the 96 wells, there are only 20 matrix conductors required.

As another example in Table 1, for a 384 well plate, using a conventional unique pair of first and second conductors for each of the 384 pairs of electrodes for the 384 wells, there are 768 first and second electrodes required. In contrast, for a 384 well plate, using a matrix of conductors of the invention for the 384 pairs of electrodes for the 384 wells, there are only 40 matrix conductors required.

In Table 2 below, each row in the table is for a respective multi-well plate, and each row in the table shows a savings in the number conductors when comparing the number of conventional first and second conductors that are needed in contrast with the respective number of matrix conductors of the invention.

For example, in Table 2, for a 96 well plate which requires 96 pairs of electrodes, using the matrix of conductors of the invention requires 172 less conductors than using a unique pair of conventional first and second conductors for each of the 96 pairs of electrodes.

As another example in Table 2, for a 384 well plate which requires 384 pairs of electrodes, using the matrix of conductors of the invention requires 728 less conductors than using a unique pair of conventional first and second conductors for each of the 384 pairs of electrodes.

TABLE 1

| No. of Wells in Plate | No. of First and Second Conductors | No. of Matrix Conductors |
|---|---|---|
| 8 | 16 | 2 + 4 = 6 |
| 96 | 192 | 8 + 12 = 20 |
| 192 | 384 | 12 + 16 = 28 |
| 288 | 576 | 16 + 18 = 34 |
| 384 | 768 | 16 + 24 = 40 |
| 768 | 1536 | 24 + 32 = 56 |

TABLE 2

| No. of Wells in Plate | Savings in the No. of Conductors Between the No. of First and Second Conductors and the No. of Matrix Conductors |
|---|---|
| 8 | 16 − 6 = 10 |
| 96 | 192 − 20 = 172 |
| 192 | 384 − 28 = 356 |
| 288 | 576 − 34 = 542 |
| 384 | 768 − 40 = 728 |
| 768 | 1536 − 56 = 1480 |

One embodiment of the multiple electrode pair array of the invention can be used with separate standard disposable rectangular well 96 well microplates such as made by Innovative Microplate, Chicopee, Mass., USA, particularly, Microplate Model S30012.

The 96 pairs of rectangular electrodes which fit into the respective 96 wells of the separate microplate are rectangular electrodes made by Keystone, specifically Keystone Part No. 1289, without holes.

Generally, the components of the multiple electrode pair array of the invention can be made from inexpensive and durable metal and plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a multiple electrode pair array with a two-dimensional matrix array of electrode conductors that is low in cost, relatively simple in design and operation, and which may advantageously be used to provide an electroporation apparatus that considerably reduces the complexity with respect to first or second electrode conductors and the complexity with respect to the electronic apparatus needed to drive first or second electrode conductors for a well plate used for electroporation. With the invention, a multiple electrode pair array and two-dimensional matrix array of electrode conductors provides an electroporation apparatus in which the number of conductors connected with electrodes for electroporation is considerably less than the number of electrodes. With the invention, a multiple electrode pair array and two-dimensional matrix array of electrode conductors provides an electroporation apparatus in which electrode pairs in all wells in a well plate can be treated with a different electrical modality. With the invention, a multiple electrode pair array and two-dimensional matrix array of electrode conductors provides an electroporation apparatus in which all pairs of electrodes in all wells in a well plate can be treated with a different electrical modality without the need for a pair of electrical conductors for each electrode pair. With the invention, a multiple electrode pair array and two-dimensional matrix array of electrode conductors provides an electroporation apparatus in which multiple electrodes are not disposed of when a multiple well plate is disposed of. With the invention, a multiple electrode pair array and two-dimensional matrix array of electrode conductors provides an electroporation apparatus in which simple, plastic disposable multi-well plates can be employed and disposed of readily. With the invention, a multiple electrode pair array and two-dimensional matrix array of electrode conductors provides a support for electrodes that are placed in the wells of a standard well plate wherein the electrode support allows access to the wells when the electrodes are positioned in the wells. With the invention, a multiple electrode pair array with a two-dimensional matrix array of electrode conductors provides that pairs of rectangular electrodes are placed into the rectangular wells of a multi-well plate so that the rectangular electrodes closely fit against adjacent walls of the wells.

The multiple electrode pair array 10 can also include alignment means, e. g. alignment pins or an alignment ridge (not shown) for receipt in complementary alignment means, e. g. pin-reception alignment wells or a ridge-reception groove located in the APPARATUS FOR RECEIVING AND ALIGNING A MULTIPLE ELECTRODE PAIR ARRAY AND A MULTIPLE TREATMENT CELL FOR USE IN ELECTROPORATION. The alignment pins can provide both alignment and electrical connection between the multiple electrode pair array 10 and the apparatus for receiving and aligning a multiple electrode pair array and a multiple treatment cell used in electroporation.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

What is claimed is:

1. A multiple electrode pair array apparatus for use with a separate multiple well plate having multiple nonconductive wells distributed in a two-dimensional matrix array having R rows and C columns, wherein the nonconductive wells are separated by walls having a wall thickness, comprising:

a non-conductive base member, an array of pairs of electrodes attached to said base member and projecting therefrom, wherein said pairs of electrodes are distributed on said base member in a two-dimensional matrix array having R rows and C columns to enable registration with the separate two-dimensional matrix array of nonconductive wells and registration with the nonconductive walls having a wall thickness, wherein each pair of electrodes includes a respective first electrode and a respective second electrode, an array of R row conductors attached to said non-conductive base member, wherein each row conductor is electrically connected to corresponding first electrodes in a corresponding row of first electrodes, and an array of C column conductors attached to said non-conductive base member, wherein said C column conductors are perpendicular to said R row conductors, wherein each column conductor is electrically insulated from said row conductors, wherein each column conductor is electrically connected to corresponding second electrodes in a corresponding column of second electrodes, wherein an adjacent electrode pair spacing gap, which is substantially equal to the nonconductive wall thickness of the multiple nonconductive wells, is provided between a first electrode on one pair of electrodes and second electrode on an adjacent pair of electrodes, such that an inside wall of the multiple well plate is received in said adjacent electrode pair spacing gap with a friction fit.

2. The apparatus of claim 1 wherein:
said first electrodes and said second electrodes are parallel to each other,
said first electrodes and said R row conductors are parallel to each other, and
said second electrodes and said C column conductors are perpendicular to each other.

3. The apparatus of claim 1 wherein:
said non-conductive base member has a top portion and a bottom portion,
said row conductors and said column conductors are positioned away from the top portion of the said non-conductive base member.

4. The apparatus of claim 1 wherein said base member includes a plurality of access channels which are in registration with the wells of the multiple well plate.

5. The apparatus of claim 4 wherein said access channels are circular in shape.

6. A combination multiple electrode pair array and a multiple well plate apparatus, comprising:

a multiple well plate having multiple nonconductive wells distributed in a two-dimensional matrix array having R rows and C columns, wherein the nonconductive wells are separated by walls having a wall thickness, and a multiple electrode pair array, separable from said multiple well plate, which includes, a non-conductive base member, an array of pairs of electrodes attached to said base member and projecting therefrom, wherein said pairs of electrodes are distributed on said base member in a two-dimensional matrix array having R rows and C columns to enable registration with said separable two-dimensional matrix array of nonconductive wells and registration with the nonconductive walls having a wall thickness, wherein each pair of electrodes includes a respective first electrode and a respective second electrode, an array of R row conductors attached to said non-conductive base member, wherein each row conductor is electrically connected to corresponding first electrodes in a corresponding row of first electrodes, and an array of C column conductors attached to said non-conductive base member, wherein said C column conductors are perpendicular to said R row conductors, wherein each column conductor is electrically insulated from said row conductors, and wherein each column conductor is electrically connected to corresponding second electrodes in a corresponding column of second electrodes, wherein an adjacent electrode pair spacing gap, which is substantially equal to the nonconductive wall thickness, is provided between a first electrode on one pair of electrodes and second electrode on an adjacent pair of electrodes, such that an inside wall of the multiple well plate, having a wall thickness, is received in said adjacent electrode pair spacing gap with a friction fit.

* * * * *